United States Patent
Kumar et al.

(10) Patent No.: US 8,841,499 B2
(45) Date of Patent: Sep. 23, 2014

(54) METHODS AND APPARATUSES FOR ISOMERIZATION OF PARAFFINS

(71) Applicant: UOP LLC, Des Plaines, IL (US)

(72) Inventors: Manoj Kumar, Gurgaon (IN); David James Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 110 days.

(21) Appl. No.: 13/672,256

(22) Filed: Nov. 8, 2012

(65) Prior Publication Data

US 2014/0128649 A1    May 8, 2014

(51) Int. Cl.
  *C07C 5/22*    (2006.01)
  *C07C 5/27*    (2006.01)

(52) U.S. Cl.
  CPC ....................................... *C07C 5/277* (2013.01)
  USPC ............................ 585/302; 585/736; 585/738

(58) Field of Classification Search
  USPC .......... 585/301, 302, 304, 734–751; 208/133, 208/134
  See application file for complete search history.

(56) References Cited

U.S. PATENT DOCUMENTS

| | | | | |
|---|---|---|---|---|
| 2,404,923 | A | * | 7/1946 | Patterson ....................... 585/738 |
| 4,190,520 | A | * | 2/1980 | Gewartowski .................. 208/95 |
| 5,227,554 | A | * | 7/1993 | Chou ............................. 585/303 |
| 5,326,926 | A | * | 7/1994 | Rice .............................. 585/738 |
| 5,649,281 | A | | 7/1997 | Sampath |
| 2009/0320370 | A1 | | 12/2009 | Fecteau et al. |

FOREIGN PATENT DOCUMENTS

WO    2012/073618 A1    6/2012

OTHER PUBLICATIONS

Ogorman, E. K., "Tenneco (Oil Co.) Upgrades Natural Gasoline," 65th Gas Process. Assoc. Annu. Conv. (San Antonio Mar. 10-12, 1986) (Adapt.) Oil Gas J. (ISSN 0030-1388) V84 N.32 100-2 (Aug. 11, 1986), v 84, n 32, p. 100-2, Mar. 10, 1986.

"New Dubai Refinery to Export Gasoline," International Journal of Hydrocarbon Engineering (ISSN 1364-3177) V3 N. 7 3 (Jul.-Aug. 1998), v 3, n 7, p. 3, Jul. 1998.

Rabeau, et al., "An Efficient Initialization Procedure for the Simulation and Optimization of Large Distillation Problems," Industrial & Engineering Chemistry Research (ISSN 0888-5885) V36 N.10 4291-98 (Oct. 1997), v 36 n 10, p. 4291-98, Oct. 1997.

Santiago, et al., "Adapting a Depropanizer Column for use as a Gasoline Depentanizer (Adapting a Depropanizer Column for use as a Gasoline Depentanizer)," Revista del Instituto Mexicano del Petroleo (ISSN 0538-1428) V24 N.2 30-35,128 (Apr.-Jun. 1992), v 24, n 2, p. 30-35,128, Apr. 1992.

(Continued)

*Primary Examiner* — Thuan D Dang
(74) *Attorney, Agent, or Firm* — Maryann Maas

(57) ABSTRACT

Embodiments of methods and apparatuses for isomerization of paraffins are provided. In one example, a method comprises the steps of compressing a $C_4^-$ hydrocarbons-containing stabilizer vapor stream to form a compressed $C_4^-$ hydrocarbons-containing stabilizer stream. A $C_4$ hydrocarbons-containing feed stream that comprises unbranched $C_4$ hydrocarbons is contacted with a chloride-promoted isomerization catalyst in the presence of hydrogen to form a branched $C_4$ hydrocarbons-containing reaction zone effluent. At least a portion of the compressed $C_4^-$ hydrocarbons-containing stabilizer stream is combined with the branched $C_4$ hydrocarbons-containing reaction zone effluent to form a $C_4$ hydrocarbons-containing combined stream. The $C_4$ hydrocarbons-containing combined stream is separated into a $C_3^-$ hydrocarbons-containing stabilizer vapor stream and a $C_4$ hydrocarbons-rich product stream that comprises branched $C_4$ hydrocarbons.

18 Claims, 2 Drawing Sheets

(56) References Cited

OTHER PUBLICATIONS

Santiago, et al., "Adapting a Depropanizer Column for use as a Gasoline Depentanizer (Adapting a Depropanizer Column for use as a Gasoline Depentanizer)," Revista del Instituto Mexicano del Petroleo (ISSN 0538-1428) V24 N.2 30-35,128 (Apr.-Jun. 1992), v 24, n 2, p. 30-35,128, Apr. 1992. (Translation).

* cited by examiner

METHODS AND APPARATUSES FOR ISOMERIZATION OF PARAFFINS

TECHNICAL FIELD

The technical field relates generally to methods and apparatuses for isomerization of hydrocarbons, and more particularly relates to methods and apparatuses for isomerization of paraffins with recovery of $C_4$ hydrocarbons.

BACKGROUND

Isomerization processes are widely used by many refiners to rearrange the molecular structure of straight chain paraffinic hydrocarbons to more highly branched hydrocarbons. Generally, these more highly branched hydrocarbons have relatively high octane ratings.

Paraffin feeds for $C_5/C_6$ hydrocarbons isomerization processes can contain cyclic $C_6^+$ hydrocarbons such as benzene and cyclic $C_7^+$ hydrocarbons. As used herein, $C_x$ hydrocarbons means hydrocarbon molecules that have "X" number of carbon atoms, $C_x^+$ hydrocarbons means hydrocarbon molecules that have "X" and more than "X" number of carbon atoms, and $C_x^-$ hydrocarbons means hydrocarbon molecules that have "X" and less than "X" number of carbon atoms. As used herein, $C_5/C_6$ hydrocarbons mean $C_5$ hydrocarbons and/or $C_6$ hydrocarbons. When the weight percent of cyclic $C_6^+$ hydrocarbons in the paraffin feed is about 20% or greater (also referred to as an X-factor of 20 or greater in which the X-factor is defined as the sum of the weight percent of the cyclic $C_6$ hydrocarbons plus $C_7^+$ hydrocarbons in the feed, e.g., benzene+cyclohexane+methylcyclopentane+$C_7^+$), the paraffin feed is considered a "hard feed to isomerize." In particular, the $C_7^+$ hydrocarbons and to a much lesser extent $C_5$ and $C_6$ hydrocarbons in the reactor tend to hydrocrack, producing $C_4$ hydrocarbons as well as other lighter hydrocarbons, e.g., $C_3^-$ hydrocarbons. The $C_4$ hydrocarbons have significant caloric and economic value. Unfortunately, the $C_4$ hydrocarbons are traditionally removed in an off-gas stream of $C_5/C_6$ hydrocarbons isomerization processes and burned because the investment and operating costs for recovering the $C_4$ hydrocarbons are prohibitively expensive.

Accordingly, it is desirable to provide methods and apparatuses for isomerization of paraffins including recovery of $C_4$ hydrocarbons with reduced overall investment and/or operating costs. Moreover, it is desirable to provide methods and apparatuses for isomerization of paraffins including recovery of $C_4$ hydrocarbons, such as for $C_5/C_6$ hydrocarbons isomerization processes that have paraffinic feed streams that may contain some $C_7^+$ hydrocarbons. Furthermore, other desirable features and characteristics of the present invention will become apparent from the subsequent detailed description and the appended claims, taken in conjunction with the accompanying drawings and this background.

BRIEF SUMMARY

Methods and apparatuses for isomerization of paraffins are provided herein. In accordance with an exemplary embodiment, a method for isomerization of paraffins comprises the steps of compressing a $C_4^-$ hydrocarbons-containing stabilizer vapor stream to form a compressed $C_4^-$ hydrocarbons-containing stabilizer stream. A $C_4$ hydrocarbons-containing feed stream that comprises unbranched $C_4$ hydrocarbons is contacted with a chloride-promoted isomerization catalyst in the presence of hydrogen to form a branched $C_4$ hydrocarbons-containing reaction zone effluent. At least a portion of the compressed $C_4^-$ hydrocarbons-containing stabilizer stream is combined with the branched $C_4$ hydrocarbons-containing reaction zone effluent to form a $C_4$ hydrocarbons-containing combined stream. The $C_4$ hydrocarbons-containing combined stream is separated into a $C_3^-$ hydrocarbons-containing stabilizer vapor stream and a $C_4$ hydrocarbons-rich product stream that comprises branched $C_4$ hydrocarbons.

In accordance with another exemplary embodiment, a method for isomerization of paraffins is provided. The method comprises the steps of contacting a $C_5^+$ hydrocarbons-containing feed stream that comprises unbranched $C_5/C_6$ hydrocarbons with a chloride-promoted isomerization catalyst in the presence of hydrogen to form a branched $C_5^+$ hydrocarbons-containing reaction zone effluent. The branched $C_5^+$ hydrocarbons-containing reaction zone effluent is separated into a $C_4^-$ hydrocarbons-containing stabilizer vapor stream and a $C_5^+$ hydrocarbon-rich product stream that comprises branched $C_5^+$ hydrocarbons. The $C_4^-$ hydrocarbons-containing stabilizer vapor stream is compressed to form a compressed $C_4^-$ hydrocarbons-containing stabilizer stream. The compressed $C_4^-$ hydrocarbons-containing stabilizer stream is cooled to form a cooled, compressed $C_4^-$ hydrocarbons-containing stabilizer stream. The cooled, compressed $C_4^-$ hydrocarbons-containing stabilizer stream is separated into a $C_4$ hydrocarbons-containing liquid stream and a $C_3^-$ hydrocarbons-containing off gas stream. The $C_4$ hydrocarbons-containing liquid stream is combined with a branched $C_4$ hydrocarbons-containing reaction zone effluent to form a $C_4$ hydrocarbons-containing combined stream. The $C_4$ hydrocarbons-containing combined stream is separated into a $C_3^-$ hydrocarbons-containing stabilizer vapor stream and a $C_4$ hydrocarbons-rich product stream that comprises branched $C_4$ hydrocarbons.

In accordance with another exemplary embodiment, an apparatus for isomerization of paraffins is provided. The apparatus comprises a compressor that is configured to receive and compress a $C_4^-$ hydrocarbons-containing stabilizer vapor stream to form a compressed $C_4^-$ hydrocarbons-containing stabilizer stream. A reaction zone contains a chloride-promoted isomerization catalyst in the presence of hydrogen. The reaction zone is configured to receive a $C_4$ hydrocarbons-containing feed stream that comprises unbranched $C_4$ hydrocarbons and to operate at isomerization conditions effective to form a branched $C_4$ hydrocarbons-containing reaction zone effluent. The apparatus is configured to combine at least a portion of the compressed $C_4^-$ hydrocarbons-containing stabilizer stream and the branched $C_4$ hydrocarbons-containing reaction zone effluent to form a $C_4$ hydrocarbons-containing combined stream. A stabilizer zone is configured to receive and separate the $C_4$ hydrocarbons-containing combined stream into a $C_3^-$ hydrocarbons-containing stabilizer vapor stream and a $C_4$ hydrocarbons-rich product stream that comprises branched $C_4$ hydrocarbons.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
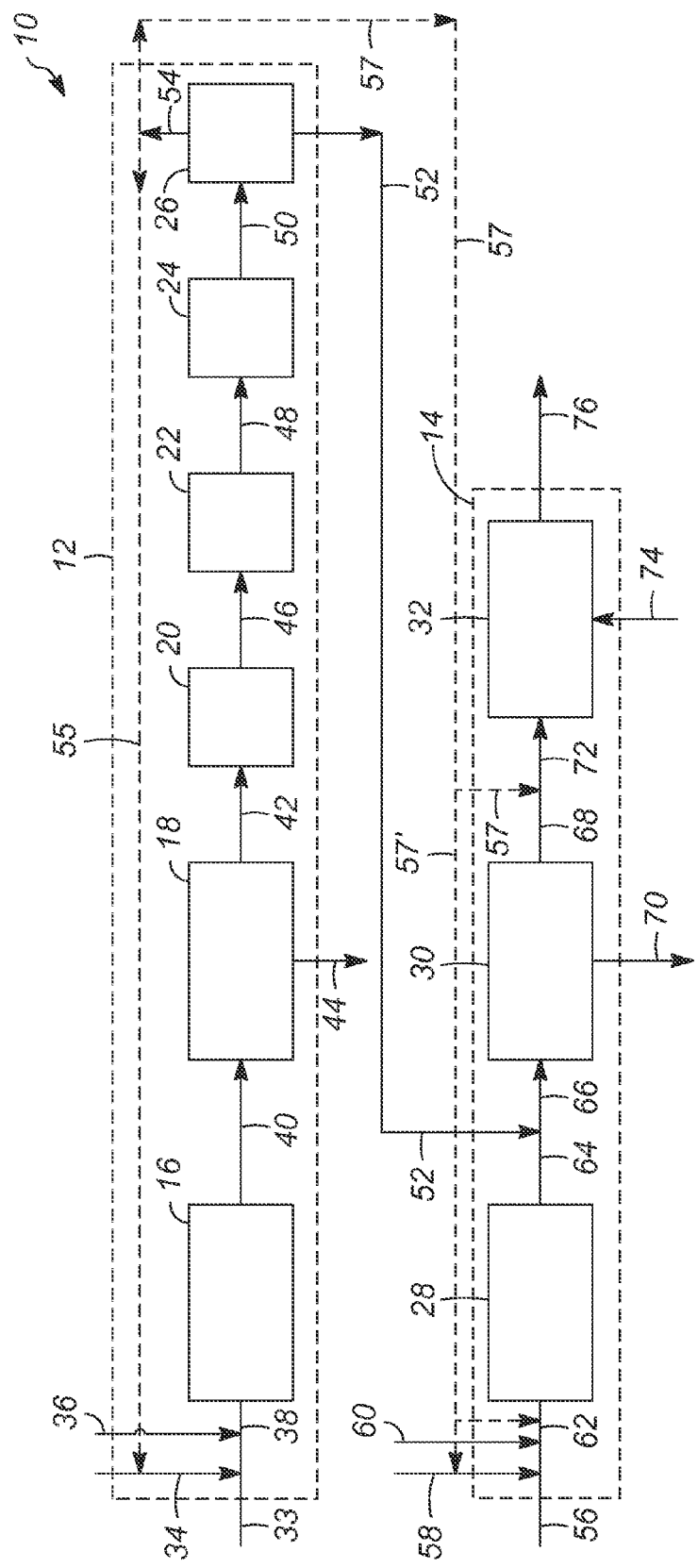
FIG. 1 schematically illustrates an apparatus and method for isomerization of paraffins in accordance with an exemplary embodiment.

The following detailed description is merely exemplary in nature and is not intended to limit the various embodiments or the application and uses thereof. Furthermore, there is no intention to be bound by any theory presented in the preceding background or the following detailed description.

Various embodiments contemplated herein relate to methods and apparatuses for isomerization of paraffins. Unlike the prior art, the exemplary embodiments of the apparatus taught herein integrate a $C_5/C_6$ hydrocarbons isomerization section with a $C_4$ hydrocarbons isomerization section. In the $C_5/C_6$ hydrocarbons isomerization section, a $C_5^+$ hydrocarbons-containing feed stream that comprises unbranched $C_5/C_6$ hydrocarbons is contacted with a chloride-promoted isomerization catalyst in the presence of hydrogen in a first reaction zone to form a branched $C_5^+$ hydrocarbons-containing reaction zone effluent. As used herein, the term "zone" refers to an area including one or more equipment items and/or one or more sub-zones. Equipment items can include one or more reactors or reactor vessels, heaters, exchangers, dryers, pipes, pumps, compressors, and controllers. Additionally, an equipment item, such as a reactor, dryer, or vessel, can further include one or more zones or sub-zones.

In an exemplary embodiment, the branched $C_5^+$ hydrocarbons-containing reaction zone effluent is introduced to a first stabilizer zone and separated into a $C_4$ hydrocarbons-containing stabilizer vapor stream and a $C_5^+$ hydrocarbon-rich product stream that comprises branched $C_5^+$ hydrocarbons. The $C_4^-$ hydrocarbons-containing stabilizer vapor stream comprises $C_4$ hydrocarbons, $C_3^-$ hydrocarbons, hydrogen, and HCl. The $C_4^-$ hydrocarbons-containing stabilizer vapor stream is compressed to form a compressed $C_4^-$ hydrocarbons-containing stabilizer stream.

In the $C_4$ hydrocarbons isomerization section, a $C_4$ hydrocarbons-containing feed stream that comprises unbranched $C_4$ hydrocarbons is contacted with a chloride-promoted isomerization catalyst in the presence of hydrogen in a second reaction zone to form a branched $C_4$ hydrocarbons-containing reaction zone effluent. In an exemplary embodiment, at least a portion of the compressed $C_4^-$ hydrocarbons-containing stabilizer stream from the $C_5/C_6$ hydrocarbons isomerization section is introduced to and combined with the branched $C_4$ hydrocarbons-containing reaction zone effluent to form a $C_4$ hydrocarbons-containing combined stream. The $C_4$ hydrocarbons-containing combined stream is separated in a second stabilizer into a $C_3^-$ hydrocarbons-containing stabilizer vapor stream and a $C_4$ hydrocarbons-rich product stream. In an exemplary embodiment, the $C_4$ hydrocarbons-rich product stream contains both branched and unbranched $C_4$ hydrocarbons correspondingly from the $C_4$ hydrocarbons isomerization section and the $C_5/C_6$ hydrocarbons isomerization section. The $C_3^-$ hydrocarbons-containing stabilizer vapor stream comprises $C_3$ hydrocarbons, hydrogen, and HCl. In an exemplary embodiment, the $C_3^-$ hydrocarbons-containing stabilizer vapor stream is introduced to a scrubbing zone and is scrubbed with a caustic to neutralize HCl. The neutralized $C_3^-$ hydrocarbons-containing stabilizer vapor stream is removed and may be burned as fuel gas.

Currently, some refiners employ separate isomerization processes for their operations, one for $C_5/C_6$ hydrocarbons isomerization and another for $C_4$ hydrocarbons isomerization. These isomerization processes often utilize correspondingly similar but independent equipment items, such as equipment for the scrubbing zones, which can have significant investment and operational cost. By integrating the $C_5/C_6$ hydrocarbons isomerization section with the $C_4$ hydrocarbons isomerization section in accordance with the various embodiments described herein, the $C_4$ hydrocarbons in the $C_4^-$ hydrocarbons-containing stabilizer vapor stream from the $C_5/C_6$ hydrocarbons isomerization section can be recovered in the $C_4$ hydrocarbons isomerization section. Additionally, in an exemplary embodiment, the single scrubbing zone in the $C_4$ hydrocarbons isomerization section can be used to neutralize HCl from both the $C_5/C_6$ hydrocarbons isomerization section and the $C_4$ hydrocarbons isomerization section, thereby eliminating a separate scrubbing zone for the $C_5/C_6$ hydrocarbons isomerization process. As such, the total investment and operating costs for the isomerization process can be reduced compared to the total investment and operating costs for two separate isomerization processes, one for $C_5/C_6$ hydrocarbons isomerization and another for $C_4$ hydrocarbons isomerization.

Referring to FIG. 1, a schematic depiction of an apparatus 10 for isomerization of paraffins in accordance with an exemplary embodiment is provided. The apparatus 10 is utilized for a paraffin isomerization process that converts normal paraffins to branched paraffins. As illustrated, the apparatus 10 comprises a $C_5/C_6$ hydrocarbons isomerization section 12 and a $C_4$ hydrocarbons isomerization section 14 that is in fluid communication with the $C_5/C_6$ hydrocarbons isomerization section 12.

In an exemplary embodiment, the $C_5/C_6$ hydrocarbons isomerization section 12 comprises a reaction zone 16, a stabilizer zone 18, a compression suction drum 20, a compressor 22, a cooler 24, and a separator 26 that are in fluid communication. The $C_4$ hydrocarbons isomerization section 14 comprises a reaction zone 28, a stabilizer zone 30, and a scrubbing zone 32 that are in fluid communication.

A $C_5^+$ hydrocarbons-containing feed stream 33 is introduced to the $C_5/C_6$ hydrocarbons isomerization section 12. The $C_5^+$ hydrocarbons-containing feed stream 33 comprises normal or unbranched paraffinic $C_5/C_6$ hydrocarbons, such as normal pentane and normal hexane. In an exemplary embodiment, the $C_5^+$ hydrocarbons-containing feed stream 33 is relatively rich in $C_5/C_6$ hydrocarbons and further comprises cyclic $C_6^+$ and $C_7^+$ hydrocarbons. In one example, the $C_5^+$ hydrocarbons-containing feed stream 33 comprises the cyclic $C_6^+$ and $C_7^+$ hydrocarbons in an amount of about 10 weight percent (wt. %) or greater, such as from about 10 to about 50 wt. % or greater, for example from about 20 to about 30 wt. %, of the $C_5^+$ hydrocarbons-containing feed stream 33. As such, the $C_5^+$ hydrocarbons-containing feed stream 33 is considered a feed stream that is "hard to isomerize," which can result in some hydrocracking of the cyclic $C_6^+$ and $C_7^+$ hydrocarbons during the isomerization of the $C_5/C_6$ hydrocarbons, thereby producing $C_4^-$ hydrocarbons.

A hydrogen-containing gas feed 34 and a chloride promoter stream 36 (e.g., containing perchloroethylene or the like) are introduced to the $C_5^+$ hydrocarbons-containing feed stream 33 to form a combined stream 38. Although not illustrated, the $C_5^+$ hydrocarbons-containing feed stream 33, the hydrogen-containing gas feed 34, the chloride promoter stream 36, and/or the combined stream 38 may be passed through a dryer(s), a heat exchanger(s), and/or a heater(s) so that the combined stream 38 is dry and heated while advancing through the reaction zone 16. In an exemplary embodiment, the combined stream 38 is at a temperature of about 90 to about 210° C. in the reaction zone 16.

In an exemplary embodiment, the reaction zone 16 comprises a fixed-bed catalytic reactor operating at a temperature of from about 90 to about 210° C. and contains an isomerization catalyst that is activated by HCl by the decomposition of chloride promoter from the chloride promoter stream 36 to form a high-activity chloride-promoted isomerization catalyst. Non-limiting examples of the isomerization catalyst include alumina catalyst, platinum aluminum catalyst, and the like that can be chlorinated. The chloride-promoted isomerization catalyst in the presence of hydrogen is effective to isomerize the normal paraffins to branched paraffins (e.g., branched pentane and/or branched hexane) to produce a branched $C_5^+$ hydrocarbons-containing reaction zone effluent 40. The branched $C_5^+$ hydrocarbons-containing reaction zone effluent 40 contains branched and some unbranched $C_5/C_6$ hydrocarbons, $C_4$ hydrocarbons, $C_3$ hydrocarbons, some naphthenes and $C_7$ paraffins, hydrogen (e.g., unreacted hydrogen), HCl, and possibly other chloride-containing compounds.

The branched $C_5^+$ hydrocarbons-containing reaction zone effluent 40 is passed along to the stabilizer zone 18 and is separated at separation conditions into a $C_4^-$ hydrocarbons-containing stabilizer vapor stream 42 and a $C_5^+$ hydrocarbon-rich product stream 44. In an exemplary embodiment, the stabilizer zone 18 (e.g., stabilizer overhead receiver) is operating at a temperature of from about 30 to about 45° C. and a pressure of from about 1030 to about 1720 kPa gauge. In an exemplary embodiment, the $C_4^-$ hydrocarbons-containing stabilizer vapor stream 42 comprises $C_4$ hydrocarbons, $C_3^-$ hydrocarbons, hydrogen, and HCl. The $C_5^+$ hydrocarbon-rich product stream 44 is rich in branched $C_5^+$ hydrocarbons (e.g., $C_5/C_6$ hydrocarbons), such as branched pentanes and/or branched hexanes, and is removed from the apparatus 10 as product.

As illustrated, the $C_4^-$ hydrocarbons-containing stabilizer vapor stream 42 is passed through the compression suction drum 20 to remove mist droplets and/or deposits from the vapor stream 42 and to form a demisted, $C_4^-$ hydrocarbons-containing stabilizer vapor stream 46. In an exemplary embodiment, the demisted, $C_4^-$ hydrocarbons-containing stabilizer vapor stream 46 is introduced to the compressor 22 at a temperature of from about 30 to about 45° C. and a pressure of from about 1030 to about 1720 kPa gauge. The compressor 22 compresses the demisted, $C_4^-$ hydrocarbons-containing stabilizer vapor stream 46 to form a compressed $C_4^-$ hydrocarbons-containing stabilizer stream 48. In an exemplary embodiment, the compressor 22 pressurizes the vapor stream 46 to forms the compressed $C_4^-$ hydrocarbons-containing stabilizer stream 48 having a pressure of from about 2760 to about 4210 kPa gauge and a temperature of from about 70 to about 120° C.

As illustrated, the compressed $C_4^-$ hydrocarbons-containing stabilizer stream 48 is passed along to the cooler 24, which cools the compressed $C_4^-$ hydrocarbons-containing stabilizer stream 48 to form a cooled, compressed $C_4^-$ hydrocarbons-containing stabilizer stream 50. In an exemplary embodiment, the cooled, compressed $C_4^-$ hydrocarbons-containing stabilizer stream 50 has a temperature of from about 0 to about 45° C., such as from about 30 to about 45° C., and a pressure of from about 2660 to about 4140 kPa gauge. The cooled, compressed $C_4^-$ hydrocarbons-containing stabilizer stream 50 is separated in the separator 26 to form a $C_4$ hydrocarbons-containing liquid stream 52 and a $C_3^-$ hydrocarbons-containing off gas stream 54. In an exemplary embodiment, the $C_4$ hydrocarbons-containing liquid stream 52 is rich in $C_4$ hydrocarbons, e.g., branched and/or unbranched paraffinic $C_4$ hydrocarbons, a significant portion of which were formed in the reaction zone 16 due to hydrocracking of $C_7^+$ hydrocarbons contained in the $C_5^+$ hydrocarbons-containing feed stream 33. The $C_3^-$ hydrocarbons-containing off gas stream 54 comprises $C_3^-$ hydrocarbons, hydrogen, and HCl.

The $C_3^-$ hydrocarbons-containing off gas stream 54 may be divided into portions 55 and 57. In an exemplary embodiment, at least the portion 55 of the $C_3^-$ hydrocarbons-containing off gas stream 54 is recycled back to the $C_5^+$ hydrocarbons-containing feed stream 33, e.g., via direct introduction to stream 33, 34, or 38, for introduction to the reaction zone 16. As illustrated, the portion 55 of the $C_3^-$ hydrocarbons-containing off gas stream 54 is introduced to the hydrogen-containing gas feed 34, which is introduced to the $C_5^+$ hydrocarbons-containing feed stream 33 to form the combined stream 38. As such, HCl and hydrogen contained in the portion 55 of the $C_3^-$ hydrocarbons-containing off gas stream 54 helped to replenish hydrogen and chloride promoter consumed during the isomerization reaction, thereby reducing the amount of makeup hydrogen and chloride promoter needed from the hydrogen-containing gas feed 34 and the chloride promoter stream 36, respectively. In an exemplary embodiment, at least the portion 57 of the $C_3^-$ hydrocarbons-containing off gas stream 54 is passed along to the $C_4$ hydrocarbons isomerization section 14 for further processing and to neutralize HCl in the off gas stream 54 as discussed in further detail below. In an exemplary embodiment and as illustrated, at least a portion 57' of the portion 57 of the $C_3^-$ hydrocarbons-containing off gas stream 54 is introduced to the stream 58 and/or 62 to help replenish hydrogen and chloride promoter consumed during the isomerization reaction, thereby reducing the amount of makeup hydrogen and/or chloride promoter needed from the hydrogen-containing gas feed 58 and/or the chloride promoter stream 60, respectively. In an exemplary embodiment, $C_3^-$ hydrocarbons-containing off gas stream 54 is divided such that portion 55 corresponds to about 30 to about 70%, such as from about 40 to about 60%, of the mass flow rate of the $C_3^-$ hydrocarbons-containing off gas stream 54 and the portion 57 corresponds to about 30 to about 70%, such as from about 40 to about 60%, of the mass flow rate of the off gas stream 54. In this embodiment, the ratio of the portion 55 to the portion 57 is such that the $C_5/C_6$ hydrocarbons isomerization section 12 maintains a suitable material balance that is not overly weighted with light end hydrocarbons, e.g., $C_3^-$ hydrocarbons.

The $C_4$ hydrocarbons-containing liquid stream 52 is passed along to the $C_4$ hydrocarbons isomerization section 14 downstream from the reaction zone 28. Upstream from the reaction zone 28, a $C_4$ hydrocarbons-containing feed stream 56 is introduced to the $C_4$ hydrocarbons isomerization section 14. The $C_4$ hydrocarbons-containing feed stream 56 comprises normal or unbranched paraffinic $C_4$ hydrocarbons, such as normal butane. A hydrogen-containing gas feed 58 and a chloride promoter stream 60 (e.g., containing perchloroethylene or the like) are introduced to the $C_4$ hydrocarbons-containing feed stream 56 to form a combined stream 62. Although not illustrated, the $C_4$ hydrocarbons-containing feed stream 56, the hydrogen-containing gas stream 58, the chloride promoter stream 60, and/or the combined stream 62 may be passed through a dryer(s), a heat exchanger(s), and/or a heater(s) so that the combined stream 62 is dry and heated while advancing through the reaction zone 28. In an exemplary embodiment, the combined stream 38 is at a temperature of about 90 to about 210° C. in the reaction zone 16.

In an exemplary embodiment, the reaction zone 28 comprises a fixed-bed catalytic reactor operating at a temperature of from about 90 to about 210° C. and contains an isomerization catalyst that is activated by HCl by the decomposition of chloride promoter from the chloride promoter stream 60 to form a high-activity chloride-promoted isomerization catalyst as described above in relation to the reaction zone 16. The chloride-promoted isomerization catalyst in the presence of hydrogen is effective to isomerize the normal paraffins to branched paraffins (e.g., branched butane) to produce a branched $C_4$ hydrocarbons-containing reaction zone effluent 64. The branched $C_4$ hydrocarbons-containing reaction zone effluent 64 contains branched and unbranched $C_4$ hydrocarbons, $C_3^-$ hydrocarbons, hydrogen (e.g., unreacted hydrogen), HCl, and possibly other chloride-containing compounds and other hydrocarbons such as $C_5$ hydrocarbons and some trace $C_6^+$ hydrocarbons.

In an exemplary embodiment, the $C_4$ hydrocarbons-containing liquid stream 52 is combined with the branched $C_4$ hydrocarbons-containing reaction zone effluent 64 to form a $C_4$ hydrocarbons-containing combined stream 66. In an exemplary embodiment, the $C_4$ hydrocarbons-containing combined stream 66 has a pressure of from about 2000 to about 2760 kPa gauge and a temperature of from about 30 to about 150° C., such as from about 80 to about 110° C. The $C_4$ hydrocarbons-containing combined stream 66 is passed through the stabilizer zone 30 and separated into a $C_3^-$ hydrocarbons-containing stabilizer vapor stream 68 and a $C_4$ hydrocarbons-rich product stream 70. The $C_4$ hydrocarbons-rich product stream 70 is rich in $C_4$ hydrocarbons including branched $C_4$ hydrocarbons, such as branched butane or isobutane, and is removed from the apparatus 10 as product. The $C_3^-$ hydrocarbons-containing stabilizer vapor stream 68 comprises $C_3^-$ hydrocarbons, hydrogen, and HCl. In an exemplary embodiment, the $C_3^-$ hydrocarbons-containing stabilizer vapor stream 68 has a pressure of from about 1000 to about 2410 kPa gauge, such as from about 1720 to about 2410 kPa gauge, and a temperature of from about 0 (or lower, e.g., −40° C.) to about 45° C.

In an exemplary embodiment, at least the portion 57 of the $C_3^-$ hydrocarbons-containing off gas stream 54 is combined with the $C_3^-$ hydrocarbons-containing stabilizer vapor stream 68 to form a $C_3^-$ hydrocarbons-containing combined stream 72. The $C_3^-$ hydrocarbons-containing combined stream 72 comprises $C_3^-$ hydrocarbons, hydrogen, and HCl. The $C_3^-$ hydrocarbons-containing combined stream 72 is passed to the scrubbing zone 32. The scrubbing zone 32 scrubs the $C_3^-$ hydrocarbons-containing combined stream 72 by neutralizing the HCl contained therein with a caustic 74, e.g., sodium hydroxide, to form a neutralized off gas stream 76 that is removed from the apparatus 10 and may be burned as fuel gas, for example.

Figure 2:
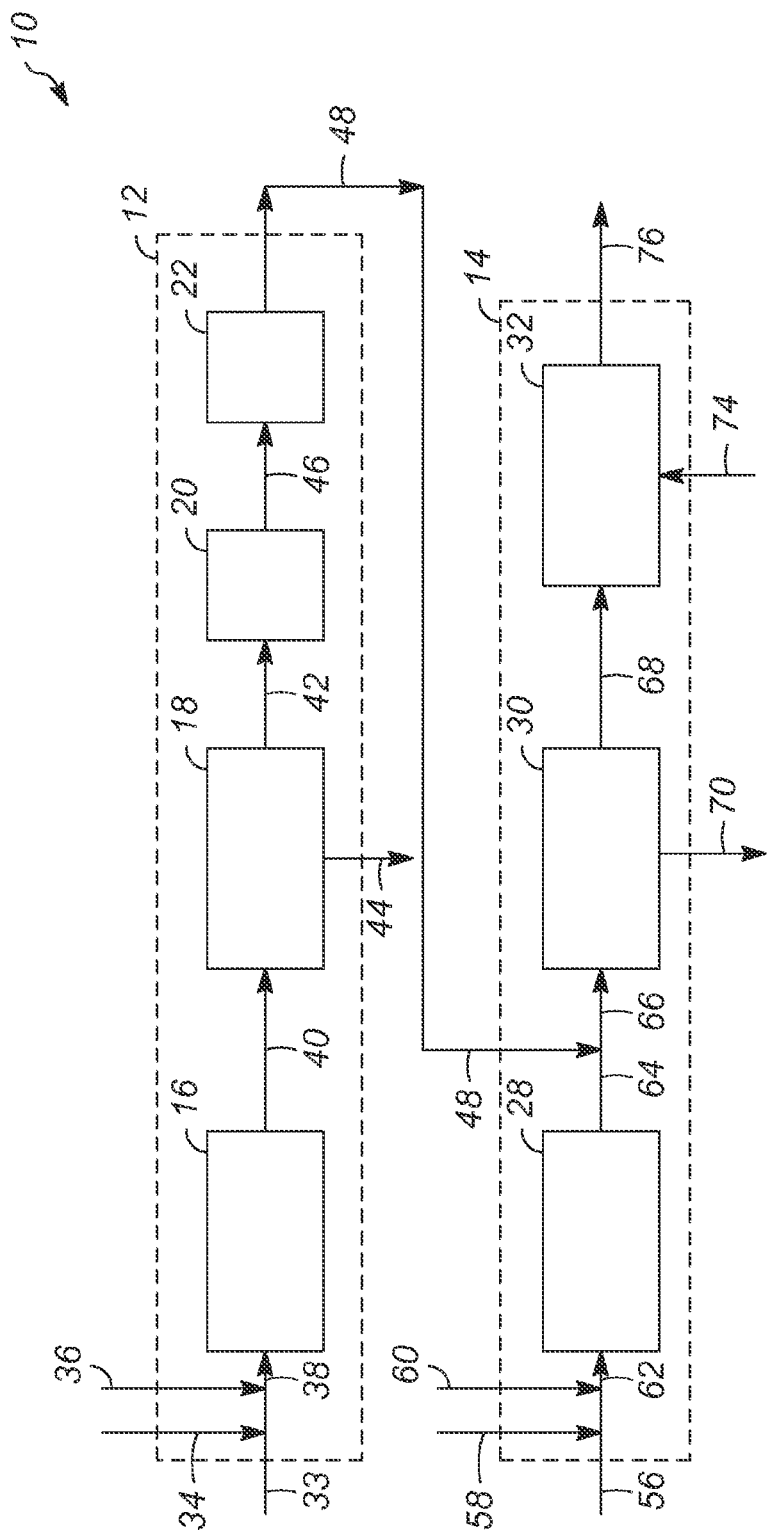
FIG. 2 schematically illustrates an apparatus and method for isomerization of paraffins in accordance with another exemplary embodiment.

Referring to FIG. 2, the apparatus 10 in accordance with another exemplary embodiment is provided. The apparatus 10 as shown in FIG. 2 is similarly configured to the apparatus 10 as shown in FIG. 1 and discussed above but without the cooler 24, the separator 26, and the resulting streams 50, 52, 54, 55, and 57. In this embodiment, the compressed $C_4^-$ hydrocarbons-containing stabilizer stream 48 from the $C_5/C_6$ hydrocarbons isomerization section 12 is passed along to the $C_4$ hydrocarbons isomerization section 14 and combined with the branched $C_4$ hydrocarbons-containing reaction zone effluent 64 to form the $C_4$ hydrocarbons-containing combined stream 66. In an exemplary embodiment, the $C_4$ hydrocarbons-containing combined stream 66 has a pressure of from about 2000 to about 2760 kPa gauge and a temperature of from about 30 to about 150° C.

As discussed above, the $C_4$ hydrocarbons-containing combined stream 66 is separated in the stabilizer zone 30 into the $C_3^-$ hydrocarbons-containing stabilizer vapor stream 68 and the $C_4$ hydrocarbons-rich product stream 70. The $C_4$ hydrocarbons-rich product stream 70 is rich in $C_4$ hydrocarbons including branched $C_4$ hydrocarbons, such as branched butane or isobutane, and is removed from the apparatus 10 as product. The $C_3^-$ hydrocarbons-containing stabilizer vapor stream 68 comprises $C_3^-$ hydrocarbons, hydrogen, and HCl. In an exemplary embodiment, the $C_3^-$ hydrocarbons-containing stabilizer vapor stream 68 has a pressure of from about 1000 to about 2410 kPa gauge, such as from about 1720 to about 2410 kPa gauge, and a temperature of from about 0 (or lower, e.g., −40° C.) to about 45° C.

In an exemplary embodiment, the $C_3^-$ hydrocarbons-containing stabilizer vapor stream 68 is passed to the scrubbing zone 32. The scrubbing zone 32 scrubs the $C_3^-$ hydrocarbons-containing stabilizer vapor stream 68 by neutralizing the HCl contained therein with the caustic 74 to form the neutralized off gas stream 76 that is removed from the apparatus 10 and may be burned as fuel gas, for example.

Accordingly, methods and apparatuses for isomerization of paraffins have been described. The exemplary embodiments taught herein integrate a $C_5/C_6$ hydrocarbons isomerization section with a $C_4$ hydrocarbons isomerization section. By integrating the $C_5/C_6$ hydrocarbons isomerization section with the $C_4$ hydrocarbons isomerization section as described herein, $C_4$ hydrocarbons contained in a stabilizer vapor stream from the $C_5/C_6$ hydrocarbons isomerization section that would otherwise be burned as fuel gas can be recovered in the $C_4$ hydrocarbons isomerization section as part of a product stream.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. A method for isomerization of paraffins, the method comprising the steps of:
   compressing a $C_4^-$ hydrocarbons-containing stabilizer vapor stream from a stabilizer overhead receiver of a $C_5/C_6$ isomerization section to form a compressed $C_4^-$ hydrocarbons-containing stabilizer stream;
   contacting, in a $C_4$ isomerization section, a $C_4$ hydrocarbons-containing feed stream that comprises unbranched $C_4$ hydrocarbons with a chloride-promoted isomerization catalyst in the presence of hydrogen to form a branched $C_4$ hydrocarbons-containing reaction zone effluent;
   combining at least a portion of the compressed $C_4^-$ hydrocarbons-containing stabilizer stream with the branched $C_4$ hydrocarbons-containing reaction zone effluent to form a $C_4$ hydrocarbons-containing combined stream; and
   separating the $C_4$ hydrocarbons-containing combined stream into a $C_3^-$ hydrocarbons-containing stabilizer vapor stream and a $C_4$ hydrocarbons-rich product stream that comprises branched $C_4$ hydrocarbons wherein, prior to the step of compressing, the $C_4^-$ hydrocarbons-containing stabilizer vapor stream is demisted to remove mist droplets and/or deposits from the $C_4^-$ hydrocarbons-containing stabilizer vapor stream.

2. The method of claim 1, wherein the step of compressing comprises compressing the $C_4^-$ hydrocarbons-containing stabilizer vapor stream to a pressure of from about 2760 to about 4210 kPa gauge to form the compressed $C_4^-$ hydrocarbons-containing stabilizer stream.

3. The method of claim 1, wherein the step of combining comprises forming the $C_4$ hydrocarbons-containing combined stream having a pressure of from about 2000 to about 2760 kPa gauge.

4. The method of claim 1, wherein the step of combining comprises forming the $C_4$ hydrocarbons-containing combined stream having a temperature of from about 30 to about 150° C.

5. The method of claim 1, wherein the step of separating comprises forming the $C_3^-$ hydrocarbons-containing stabilizer vapor stream having a pressure of from about 1000 to about 2410 kPa gauge.

6. The method of claim 1, wherein the step of separating comprises forming the $C_3^-$ hydrocarbons-containing stabilizer vapor stream having a temperature of from about −40 to about 45° C.

7. A method for isomerization of paraffins, the method comprising the steps of:

Contacting, in a $C_5/C_6$ isomerization section, a $C_5^+$ hydrocarbons-containing feed stream that comprises unbranched $C_5/C_6$ hydrocarbons with a chloride-promoted isomerization catalyst in the presence of hydrogen to form a branched $C_5^+$ hydrocarbons-containing reaction zone effluent;

separating the branched $C_5^+$ hydrocarbons-containing reaction zone effluent into a $C_4^-$ hydrocarbons-containing stabilizer vapor stream from a stabilizer overhead receiver and a $C_5^+$ hydrocarbon-rich product stream that comprises branched $C_5^+$ hydrocarbons;

compressing the $C_4^-$ hydrocarbons-containing stabilizer vapor stream to form a compressed $C_4^-$ hydrocarbons-containing stabilizer stream;

cooling the compressed $C_4^-$ hydrocarbons-containing stabilizer stream to form a cooled, compressed $C_4^-$ hydrocarbons-containing stabilizer stream; and separating the cooled, compressed $C_4^-$ hydrocarbons-containing stabilizer stream into a $C_4$ hydrocarbons-containing liquid stream and a $C_3^-$ hydrocarbons-containing off gas stream;

combining the $C_4$ hydrocarbons-containing liquid stream with a branched $C_4$ hydrocarbons-containing reaction zone effluent from a $C_4$ isomerization section to form a $C_4$ hydrocarbons-containing combined stream; and separating the $C_4$ hydrocarbons-containing combined stream into a $C_3^-$ hydrocarbons-containing stabilizer vapor stream and a $C_4$ hydrocarbons-rich product stream that comprises branched $C_4$ hydrocarbons wherein, prior to the step of compressing, the $C_4^-$ hydrocarbons-containing stabilizer vapor stream is demisted to remove mist droplets and/or deposits from the $C_4^-$ hydrocarbons-containing stabilizer vapor stream.

8. The method of claim 7, wherein the step of contacting comprises contacting the chloride-promoted isomerization catalyst with the $C_5^+$ hydrocarbons-containing feed stream that further comprises cyclic $C_6^+$ and $C_7^+$ hydrocarbons.

9. The method of claim 8, wherein the step of contacting comprises contacting the chloride-promoted isomerization catalyst with the $C_5^+$ hydrocarbons-containing feed stream that comprises the cyclic $C_6^+$ hydrocarbons and $C_7^+$ hydrocarbons in an amount of about 10 wt. % or greater of the $C_5^+$ hydrocarbons-containing feed stream.

10. The method of claim 7, wherein compressing comprises compressing the $C_4^-$ hydrocarbons-containing stabilizer vapor stream to a pressure of from about 2760 to about 4210 kPa gauge to form the compressed $C_4^-$ hydrocarbons-containing stabilizer stream.

11. The method of claim 7, wherein compressing comprises forming the compressed $C_4^-$ hydrocarbons-containing stabilizer stream having a temperature of from about 70 to about 120° C.

12. The method of claim 7, wherein the step of cooling comprises forming the cooled, compressed $C_4^-$ hydrocarbons-containing stabilizer stream having a temperature of from about 0 to about 45° C.

13. The method of claim 7, wherein the step of separating the cooled, compressed $C_4^-$ hydrocarbons-containing stabilizer stream comprises separating the cooled, compressed $C_4^-$ hydrocarbons-containing stabilizer stream at a pressure of from about 2660 to about 4140 kPa gauge.

14. The method of claim 7, wherein the step of separating the cooled, compressed $C_4^-$ hydrocarbons-containing stabilizer stream comprises separating the cooled, compressed $C_4^-$ hydrocarbons-containing stabilizer stream at a temperature of from about 0 to about 45° C.

15. The method of claim 7, further comprising the steps of:
combining at least a portion of the $C_3^-$ hydrocarbons-containing off gas stream with the $C_3^-$ hydrocarbons-containing stabilizer vapor stream to form a $C_3^-$ hydrocarbons-containing combined stream that comprises $C_3^-$ hydrocarbons, hydrogen, and HCl; and
scrubbing the $C_3^-$ hydrocarbons-containing combined stream with a caustic to neutralize HCl.

16. The method of claim 7, further comprising the steps of:
recycling at least a portion of the $C_3^-$ hydrocarbons-containing off gas stream that comprises $C_3^-$ hydrocarbons, hydrogen, and HCl back to the $C_5^+$ hydrocarbons-containing feed stream.

17. The method of claim 16, wherein the step of recycling comprises introducing that at least the portion of the $C_3^-$ hydrocarbons-containing off gas stream to the $C_5^+$ hydrocarbons-containing feed stream at from about 30 to about 70% of a mass flow rate of the $C_3^-$ hydrocarbons-containing off gas stream.

18. The method of claim 7, further comprising the steps of:
combining a $C_4$ hydrocarbons-containing feed stream that comprises unbranched $C_4$ hydrocarbons with at least a portion of the $C_3^-$ hydrocarbons-containing off gas stream that comprises $C_3^-$ hydrocarbons, hydrogen, and HCl to form a combined stream; and
contacting the combined stream with an isomerization catalyst to form the branched $C_4$ hydrocarbons-containing reaction zone effluent.

* * * * *